United States Patent
Van der Weide et al.

(10) Patent No.: US 6,649,402 B2
(45) Date of Patent: Nov. 18, 2003

(54) MICROFABRICATED MICROBIAL GROWTH ASSAY METHOD AND APPARATUS

(75) Inventors: Daniel W. Van der Weide, Madison, WI (US); Frederick R. Blattner, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 73 days.

(21) Appl. No.: 09/887,647

(22) Filed: Jun. 22, 2001

(65) Prior Publication Data

US 2002/0197709 A1 Dec. 26, 2002

(51) Int. Cl.[7] .................................................. C12M 1/34
(52) U.S. Cl. ................................. 435/288.4; 435/287.1; 435/305.2; 435/305.3
(58) Field of Search ........................... 435/285.2, 287.1, 435/288.4, 305.2, 305.3; 422/102, 82.01, 82.02; 324/448, 450; 204/403.1, 403.03

(56) References Cited

U.S. PATENT DOCUMENTS

| | | | | |
|---|---|---|---|---|
| 4,072,578 A | * | 2/1978 | Cady et al. | 435/287.1 |
| 4,123,701 A | * | 10/1978 | Josefsen et al. | 324/448 |
| 5,041,266 A | * | 8/1991 | Fox | 422/102 |
| 5,252,294 A | * | 10/1993 | Kroy et al. | 422/102 |
| 5,312,590 A | | 5/1994 | Gunasingham | |
| 5,532,128 A | | 7/1996 | Eggers et al. | |
| 5,653,939 A | | 8/1997 | Hollis et al. | |
| 5,670,322 A | | 9/1997 | Eggers et al. | |
| 5,824,494 A | * | 10/1998 | Feldberg | 435/40 |
| 5,846,708 A | | 12/1998 | Hollis et al. | |
| 5,858,666 A | | 1/1999 | Weiss | |
| 5,891,630 A | | 4/1999 | Eggers et al. | |
| 6,046,021 A | * | 4/2000 | Bochner | 435/34 |
| 6,235,520 B1 | * | 5/2001 | Malin et al. | 435/287.1 |
| 6,247,350 B1 | * | 6/2001 | Tsukuda et al. | 73/31.05 |
| 6,284,459 B1 | | 9/2001 | Nova et al. | |
| 6,370,233 B1 | * | 4/2002 | Bennett et al. | 379/37 |
| 6,436,631 B1 | * | 8/2002 | Bochner | 435/4 |

FOREIGN PATENT DOCUMENTS

| | | | | |
|---|---|---|---|---|
| DE | 10010081 A1 | * | 9/2001 | C12M/1/34 |
| GB | 2177801 A | * | 1/1987 | G01N/27/07 |
| JP | 53088387 A | * | 8/1978 | C12M/1/34 |
| JP | 09289886 A | * | 11/1997 | C12M/1/34 |
| WO | WO 200022425 A1 | * | 4/2000 | B01L/3/00 |
| WO | WO 01/57533 A2 | | 2/2001 | |

OTHER PUBLICATIONS

Bochner, "The Biolog MicroStation System and General Procedures for Identifying Envirnmental Bacteria and Yeast." Automated Microbial Identification and Quantitation: Technologies for the 2000's, Interpharm Press, Inc.: Buffalo Grove, IL, pp. 13–31 (1996).*

(List continued on next page.)

Primary Examiner—William H. Beisner
(74) Attorney, Agent, or Firm—Foley & Lardner

(57) ABSTRACT

Microbial growth assays are carried out utilizing assay apparatus having a base plate with a plurality of microbial growth assay wells, each well having a liquid content of 30 $\mu$l or less. Electrodes are coupled together through the wells and electrical connectors are connected to the electrodes to allow the effect of the content of the wells to be measured by measuring the capacitance or resistance or both between the electrodes at each well, with the change in the capacitance or resistance in each well over time being correlated with the extent of growth of a bacterium introduced into the well with a growth medium. The small size of the microwells causes the growth of bacteria in the well to quickly show a change in the electrical properties of the well, particularly in the capacitance or resistance between the electrodes at each well, with growth to saturation occurring for common bacteria such as *E. coli* in a few hours or less. High density base plates may be tested with a large variety of substances that may have an effect on the growth of the bacteria in the well over a relatively short period of time, allowing high throughput while maintaining the accuracy of the test.

21 Claims, 7 Drawing Sheets

OTHER PUBLICATIONS

P. Silley, et al., "Impedance Microbiology—a Rapid Change for Microbiologists," J. of Applied Microbiology, 1996, vol. 80, No. 3, pp. 233–243.

Lee, et al., "Rapid Preservative Efficacy Screening of Cosmetic and Personal Care Products Using Impedance Microbiology," American Society for Microbiology 101 General Meeting, Abstracts, Session No. 44/Q. Abstract Q–82, May 21, 2001, p. 599.

Toshio Tsuchiya, et al., "Rapid Automated Detection of Bacterial Growth by Impedance Measurement, and Its Application to Antibiotic Sensitivity Testing," Dept. of Clinical Pathology, Nihon Univ. School of Medicine, Nihon Univ. J. Med. vol. 20, No. 4, 1978; pp. 319–330.

Carmelo J. Felice, et al., "Impedance Bacteriometry: Medium and Interface Contributions During Bacterial Growth," Intl. Conf. IEEE Engr. in Medicine and Biology Society, vol. 12, No. 3, 1990, pp. 1027–1028.

Carmelo J. Felice, et al., "Impedance Bacteriometry: Medium and Interface Contributions During Bacterial Growth," IEEE Trans. on Biomedical Engr., vol. 39, No. 12, Dec., 1992, pp. 1310–1313.

Carmelo J. Felice, et al., "Input Amplifier Current Components in the Electrode Interface Impedancimetric Bacterial Growth Curves," Proc. 14th Int. Conf. IEEE/EMBS, Paris, France, Oct. 29–Nov. 1, 1992, pp. 2763–2764.

R.E. Madrid, et al., "Bacterial Growth Analyzer by Impedance and Trubidity," Proc. 14th Int. Conf. IEEE/EMBS, Paris, France, Oct. 29–Nov. 1, 1992, pp. 2170–2171.

Max A. Hilhorst, et al., "A Broad–Bandwidth Mixed Analog/Digital Integrated Circuit for the Measurement of Complex Impedances," IEEE J. of Solid–State Circuits, vol. 28, No. 7, Jul., 1993, pp. 764–__.

A. Singal, "Opto Electronic Biosensors for Bacteria and Viruses in Blood," Proceedings RC–IEEE–EMBS & 14th BMESI–1995, pp. SPC1–SPC2.

Jiunn Jong Wu, et al., "Rapid Detection of Oxacillin–Resistant Staphylococcus aureus in Blood Cultures by an Impedance Method," J. of Clinical Microbiology, Jun., 1997, pp. 1460–1464.

Rossana E. Madrid, et al., "Electronic Continuous Growth Follow–Up of Microbial Cultures," Proc. 19th Intl. Conf.–IEEE/EMBS, Oct. 30–Nov. 2, 1997, Chicago, Illinois, pp. 2575–2577.

K.R. Milner, et al., "Dielectrophoretic Classification of Bacteria Using Differential Impedance Measurements," Electronics Letters, vol. 34, No. 1, Jan. 1, 1998, pp. 66–68.

Ay Huey Huang, et al., "Direct Antimicrobial Susceptibility Testing of Gram–Negative Bacilli in Blood Cultures by an Electrochemical Method," J. of Clinical Microbiology, Oct., 1998, pp. 2882–2886.

C.J. Felice, et al., "Medium and Interface Components in Impedance Microbiology," IEEE Trans. on Biomedical Engineering, vol. 46, No. 12, Dec., 1999, 1483–1487.

* cited by examiner

MICROFABRICATED MICROBIAL GROWTH ASSAY METHOD AND APPARATUS

This invention was made with United States government support awarded by the following agency: DOD N00014-99-1-0717. The United States has certain rights in this invention.

FIELD OF THE INVENTION

This invention pertains generally to the field of devices and techniques for microbial growth assays and to the screening of substances for their effect on cell growth.

BACKGROUND OF THE INVENTION

Several types of microbial growth assays have been developed, some with commercial success, but most of these assays rely on flow-through chambers, large (greater than ml) sample sizes, or long incubation periods, which limits the suitability of such assays for high-throughput screening. Targeted against a range of wild-type or enfeebled strains of various pathogenic bacteria, the growth assay is the simplest and most direct measurement of drug efficacy, and represents the means by which almost all antimicrobial drugs have been discovered. The classic culture methods used by Fleming for the discovery of penicillin are still applied in clinical diagnostics today, and have been the primary path for drug discovery as well, even though response times are typically measured in days. Faster techniques that have been developed for measuring cell concentrations still employ relatively large volumes. These techniques and devices include optical measures of turbidity, flow cytometers, biomass measurements with microbalances, and electronic counting techniques, predominantly the Coulter counter. These techniques can still take hours to respond, given the large populations being measured.

Because of the small size of most bacteria, conventional optical measurements of scattering or attenuation lack the combination of speed and selectivity needed for high-density arrays, in part because the dielectric contrast between the cells and their medium is low in the visible portion of the electromagnetic spectrum. High-frequency electrical characterization, however, is attractive for microbial growth assays because it circumvents the need for image analysis and it is readily scalable to manipulating and screening sub-visible particles, such as viruses. See D. W. van der Weide, "Microscopes for the sub-visible: scanning the near field in the microwave through infrared," Optics and Photonics News, 1998, Vol. 9, pp. 40–45; D. W. E. Allsopp, et al., "Impedance technique for measuring dielectrophoretic collection of microbiological particles," Journal of Physics D (Applied Physics), 1999, Vol. 32(9), pp. 1066–74. Although it operates at low frequencies, the Coulter counter exploits the contrast in conductivity between cells and their medium as the cells traverse an aperture between two chambers: a change in resistance is a discrete event corresponding to the presence of a cell in the aperture. Other more sophisticated high-frequency techniques measure not only the real part (resistance/conductance) but also the imaginary part (reactance/susceptance) of the cells' impedance/admittance, since cells display a complex permittivity. See R. Pethig, et al., "The passive electrical properties of biological systems: their significance in physiology, biophysics and biotechnology," Phys Med Biol, 1987, Vol. 32(8), pp. 933–70; A. D. Shaw, et al., "Rapid analysis of high-dimensional bioprocesses using multivariate spectroscopies and advanced chemometrics," Adv Biochem Eng Biotechnol, 2000, Vol. 66, pp. 83–113.

A crisis in the management of infectious disease has resulted from the emergence of new pathogens and the development of resistance to old antibiotics. This crisis has generated a great need for improved antibiotic discovery techniques. Some of the potential new sources for antibiotic drugs require the testing of many thousands or millions of samples to find suitable active compounds. Current growth assay technology, which typically requires many hours or days to analyze the effectiveness of a potential new antibiotic, is not well-suited to the economic screening of potential antibiotics on such a massive scale. Reliable, rapid assays which can be carried out in a few hours or less with minimal human intervention are thus urgently needed.

SUMMARY OF THE INVENTION

In accordance with the invention, rapid assays of bacterial growth can be carried out in a very short period of time, typically in a few hours or less, to test a wide variety of substances for their effect on bacterial growth. The short time required to determine whether the substances have an effect on bacterial growth coupled with automated measurement of bacterial growth in individual samples allows very high throughput, making feasible the analysis of thousands or tens of thousands of target samples per day. Excellent growth assay accuracy is obtained by obtaining tests with samples of a selected bacterium without an inhibitor of growth, samples in which a known antibiotic is added to the bacteria and growth medium, and samples in which no bacterium is present. Only very small amounts of the substances to be tested are required for the test, minimizing the costs and allowing the evaluation of substances that are in short supply.

The microbial growth assay apparatus of the invention includes microbial growth assay wells, which may be provided in a base plate having a top surface, each well preferably having a liquid capacity of 30 microliters ($\mu$l) or less or being filled with fluid contents of 30 $\mu$l or less and preferably in the range of a few tens of nanoliters. Electrodes are coupled together through the wells, and electrical connectors are connected to the electrodes, to enable electrical measurements of the impedance of the content of each well. For example, the effect of the content of the wells may be measured by measuring the capacitance between the electrodes at each well and/or the electrodes may be formed to make conductive contact with the contents of the wells to allow measurements of the electrical resistance of the contents. The electrical measurements of the contents of each well are made over a period of time during which a cell population in the growth medium in the well may be expected to rapidly increase to provide a measurable change in the capacitance or other electrical properties measured at the well. Because of the small amount of liquid content in the wells, a small number of bacteria introduced into each well (e.g., 50–100) will rapidly multiply to a size sufficient to saturate the well in a short period of time, a few hours or less, particularly with a common bacterium such as E. coli.

To carry out multiple sample tests at a high density, a base plate is utilized which has a top surface and a plurality of microbial growth assay wells formed as depressions in the base plate which extend below the top surface, with the wells arranged in a rectangular matrix pattern, each of the wells having a liquid capacity of 30 $\mu$l or less and preferably in the range of tens of nanoliters. A first electrode for each well may be formed under the well and a second electrode for each well may be formed on a cover mounted over the base plate such that a capacitor is formed between the first and second electrodes for each well with the contents of the well between the electrodes, allowing the effect of the contents of the wells to be measured by measuring the capacitance between the electrodes at each well. The electrodes may also be formed coaxially, with an inner electrode and a coaxial outer electrode. The apparatus may further include a meter that measures capacitance and a switching unit, the switching unit electrically connected to the meter and electrically connected individually to the electrodes for each of the plurality of wells, with the switching unit switchable to selectively connect the electrodes for one of the wells at a time to the meter. The meter can measure the capacitance between the electrodes and also preferably can measure conductance and resistance between the electrodes, as appropriate. A computer may be connected to the meter and to the switching unit to provide control signals to the switching unit and the meter to control the connection of the electrodes from individual wells to the meter and to receive a signal from the meter for each well that is coordinated with the switching of the switching unit to connect the electrodes for the well to the meter. The wells may be formed in small sizes, e.g., few microns on a side, with a preferred liquid capacity range of a few tens of nanoliters, and arranged in very high density on a standard microtiter size base plate, e.g., with a well density from several hundred to several thousand wells per base plate, facilitating the rapid and simultaneous testing of a large number of different substances for their effects on bacterial growth.

Further objects, features and advantages of the invention will be apparent from the following detailed description when taken in conjunction with the accompanying drawings.

DETAILED DESCRIPTION OF THE INVENTION

Figure 1:
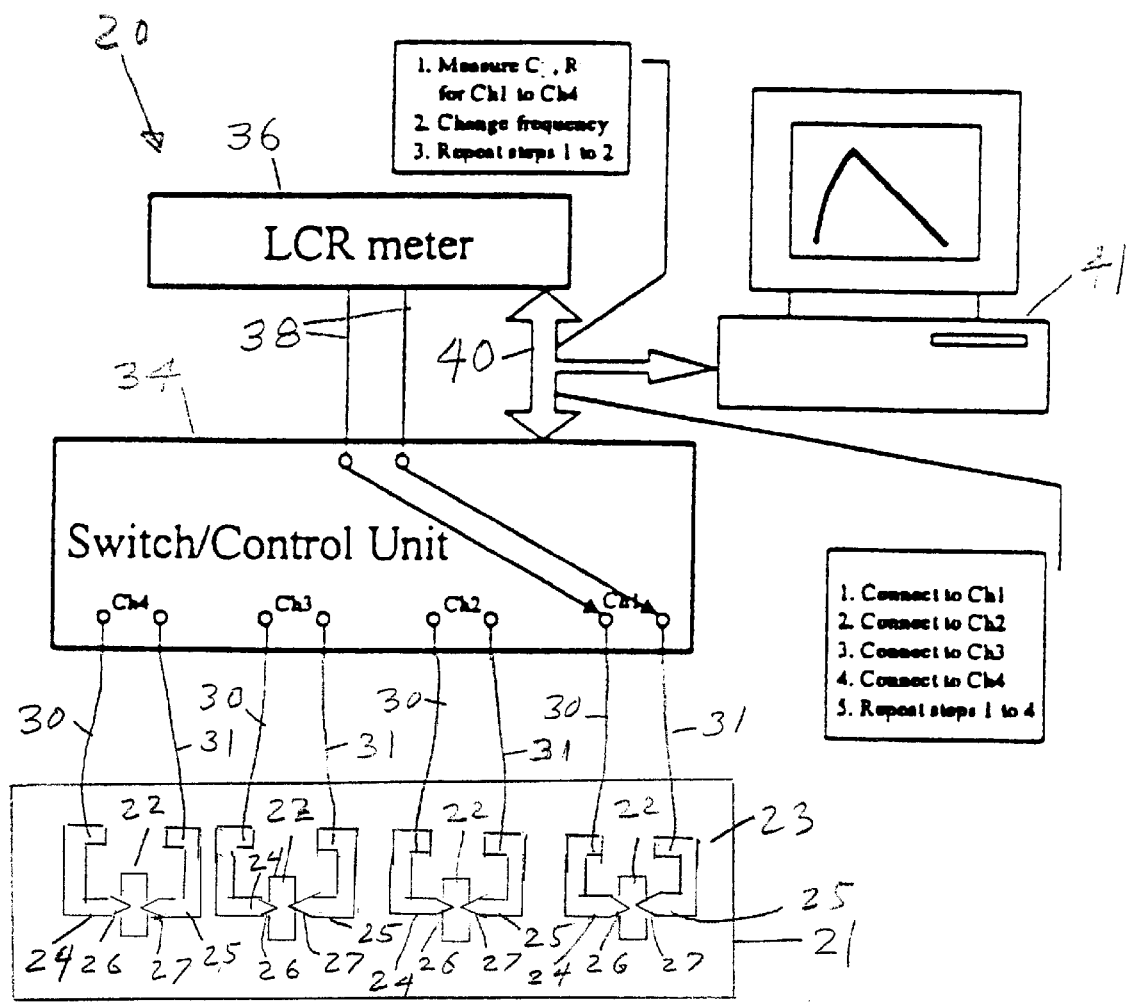
FIG. 1 is an illustrative view of microfabricated microbial growth assay apparatus in accordance with the invention.

The present invention allows rapid assays of microbial growth by utilizing very small volumes of bacteria and growth medium, preferably utilizing assay wells having a volume capacity of 30 microliters ($\mu$l) or less, and most preferably in the range of a few tens of nanoliters. The microwells of the assay apparatus in accordance with the invention may be formed in various ways. A first microbial growth assay apparatus which exemplifies the principles of the invention is shown generally at 20 in FIG. 1. The apparatus 20 includes a base plate 21 (e.g., formed of a non-reactive material such as glass, silicon, and various polymer plastics), on the top surface 23 of which are formed a plurality of growth assay wells 22 (four shown for exemplification). A first electrode 24 and a second electrode 25 are mounted on the base plate and are capacitively coupled to each other through the wells. To enhance the electric field strength, the electrodes 24 and 25 in the structure of FIG. 1 are each formed to have an apex 26 and 27, respectively, the points of which face each other across a gap within the well 22. The electrodes 24 and 25 are formed to make electrical contact with liquid contained within the wells 22 to allow measurements to be made to determine the resistance of the liquid in the gap between the electrodes as well as to determine the capacitive coupling between the electrodes 24 and 25 as affected by the liquid in the wells 22. The volume of liquid in the wells 22 is preferably less than about 30 $\mu$l, with the volume of liquid in the gap between the two apexes 26 and 27 being significantly less, generally in the range of nanoliters.

Electrical conductors (e.g., wires) 30 and 31 are connected to the first and second electrodes 24 and 25, respectively, and extend to a switch/control unit 34 which may be of conventional construction (e.g., a Hewlett-Packard Model HP3488A) or may be specially constructed (e.g., as an integrated circuit mounted on the same substrate with the electrodes). A meter 36 which is capable of measuring at least capacitance, and preferably also resistance and inductance, is connected by conductors 38 to the switch control unit 34. The meter 36 may be, for example, a precision LCR meter (e.g., a Hewlett-Packard Model HP4285A). It is understood that any commercially available or custom designed meter and switch/control unit may be utilized. The switch/control unit 34 serves to selectively connect the conductors leading to the LCR meter 36 to the conductors 30 and 31 leading to the electrodes at a selected one of the wells 22. The LCR meter 36 and the switch control unit 34 are connected by signal and control lines 40 to a computer 41. The computer 41 provides control signals to the switch/control unit 34 to sequentially connect the LCR meter 36 to the electrodes at each of the wells in sequence while controlling the LCR meter to take readings at each well, and the computer 41 receives the data from the LCR meter 36 on lines 40 and records and stores such data in the memory of the computer. Any suitable computer, including laptop and desktop computers may be utilized in a conventional fashion.

Figure 2:
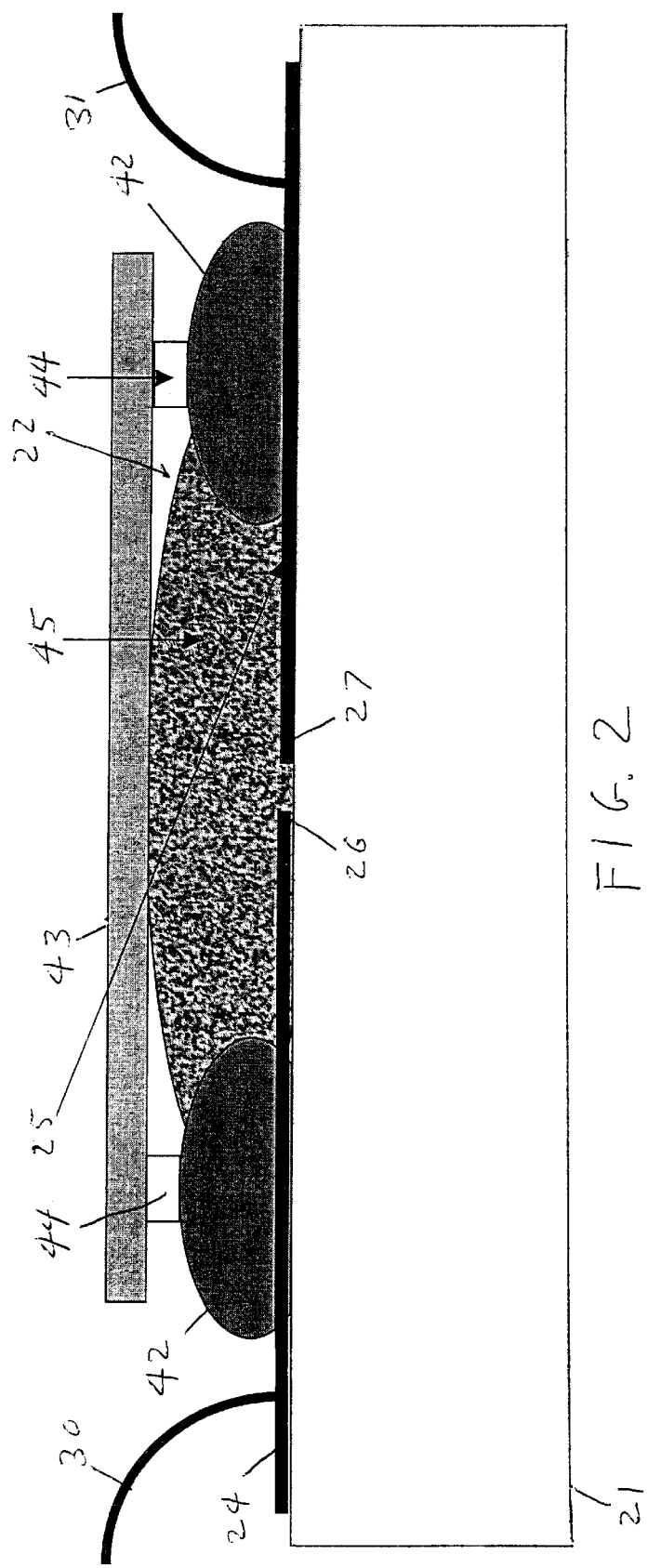
FIG. 2 is a simplified cross-sectional view through a growth assay well of the apparatus of FIG. 1.

As shown in the cross-sectional view of FIG. 2, each well 22 may be laterally defined by walls 42 of, e.g., epoxy deposited on the plate 21, with a preferably transparent plate 43 mounted over the wells 22 and sealed to the walls 42 with a sealant layer 44 such as a vacuum grease. The top surface 23, the walls 42, the sealant layer 44 and the cover plate 43 define an enclosure for a bacterial culture 45 that is held in the well 22. As seen in FIG. 2, the points of the apexes 26 and 27 of the electrodes 24 and 25 define a small gap which is occupied by the culture 45 to allow impedance measurements of the culture between the apexes 26 and 27.

As an example of the utilization of the apparatus 20 of FIGS. 1 and 2, a single colony of E. coli K-12 MG 1655 was used to inoculate five ml of Luria Broth (LB) which was grown overnight at 37° C. with constant aeration. A 1% inoculum was used to subculture in fresh LB medium and grew to $OD_{600}$ of 0.5 (measured by a Beckman DU-20 spectrophotometer). 15 μl of cell culture was mixed with 15 μl of LB medium in samples with and without ampicillin (100 μg/ml), and aliquoted into the wells 22. In addition, an equal volume of LB medium (30 μl) with ampicillin was aliquoted into an additional well to function as a negative control. Specifically, for the four well system as illustrated in FIG. 1, two wells included the selected bacteria and the growth medium free of antibiotic, one well 22 included the selected bacteria, the growth medium, and the ampicillin antibiotic, and the control well contained the growth medium and the antibiotic but no bacteria.

Figure 3:
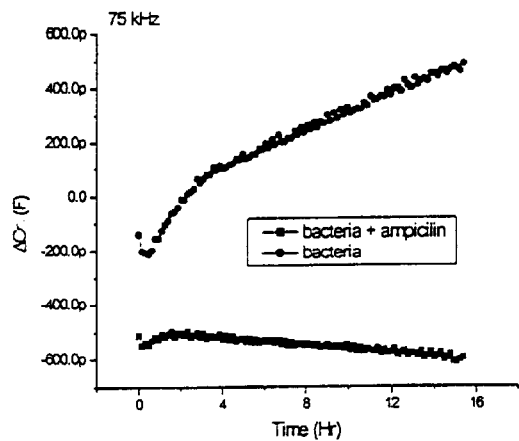
FIG. 3 are graphs showing the change in capacitance over time for a bacterial growth test utilizing the apparatus of FIG. 1 at a measurement frequency of 75 kHz.
Figure 4:
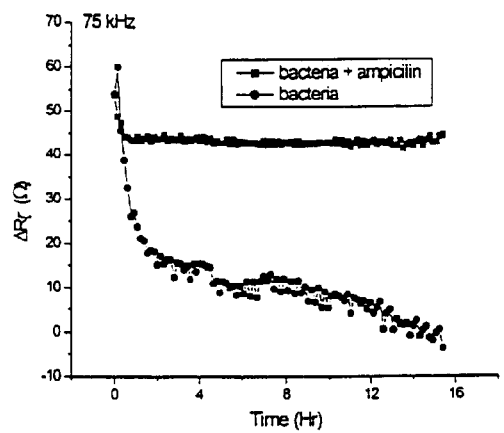
FIG. 4 are graphs showing the change in resistance over time for a bacterial growth test utilizing the apparatus from FIG. 1 at a frequency of 75 kHz.
Figure 5:
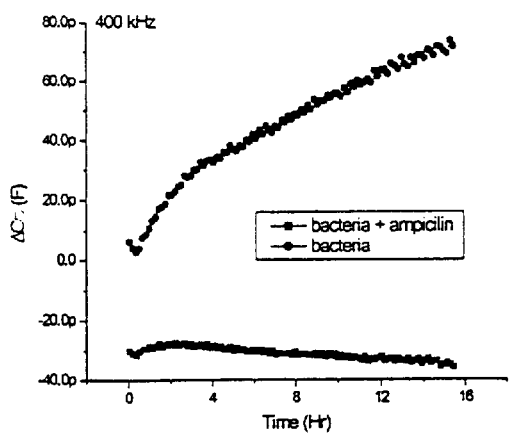
FIG. 5 are graphs showing the change in capacitance over time for a bacterial growth test utilizing the apparatus of FIG. 1 at a frequency of 400 kHz.
Figure 6:
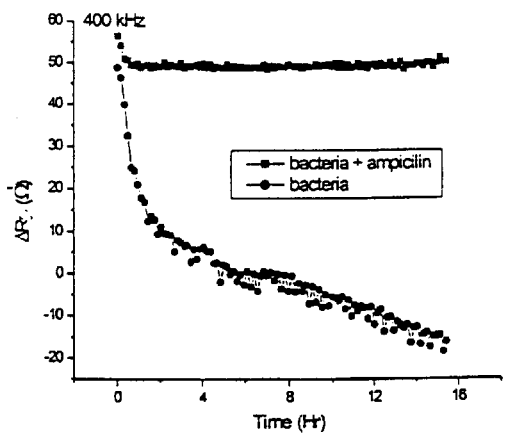
FIG. 6 are graphs showing the results of bacterial growth test utilizing the apparatus of FIG. 1 at a frequency of 400 kHz.

The measurements were carried out with the system set up as shown in FIG. 1, with the computer (PC) 41 interfaced to a Model HP4285A precision LCR meter and a Model HP3488A switch/control unit. The switch/control unit 34 was used to switch the connection of the LCR meter 36 to the conductors 30 and 31 leading to the electrodes of the wells 22 in sequence. A 10 mV rms alternating current signal of varying frequency (between 75 kHz and 30 MHz) was used for electrical excitation and was applied between the electrodes 24 and 25. The measurement frequency was swept from 75 kHz to 30 MHz in 28 uniform steps on a logarithmic scale. At each frequency, impedance (capacitance and resistance) was measured between the electrodes 24 and 25 for each of the four wells. The base plate 21 with the wells 22 and electrodes 24 and 25 thereon was kept in a Faraday cage to eliminate electrical noise pickup. The measurements were made while keeping the temperature of the base plate and of the content of the wells 22 at a physiological temperature of 37°±1° C. The values of the impedance (assuming a parallel RC equivalent circuit model, resistance and capacitance, R and C) between the electrodes 24 and 25 at each of the cells was recorded periodically over about 16 hours under the control of the computer 41. The well containing only growth medium and ampicillin was used as the control. After the impedance measurements were taken and stored in the computer 41, the relative capacitance was determined for each of the other wells with respect to the control well (growth medium containing ampicillin but no bacterium), i.e., $\Delta C = C_{bacteria} - C_{control}$ where $\Delta C$ is the relative capacitance of a well, $C_{bacteria}$ is the measure of capacitance of the well containing bacteria (with or without ampicillin), and $C_{control}$ is the capacitance measured at the control well. The results of these tests are shown in FIGS. 3–6. FIG. 3 shows the relative capacitance of a well containing bacteria only (no ampicillin) and a well containing bacteria plus ampicillin measured at 75 kHz, and FIG. 4 shows the resistance of a well containing bacteria without ampicillin and a well containing bacteria with ampicillin, again measured at 75 kHz. FIG. 5 shows relative capacitance for the two wells as measured at 400 kHz, and FIG. 6 shows relative resistance for the two wells at 400 kHz. During these tests no agitation of the contents of the wells was carried out. These data show that the capacitance between the electrodes at a well containing bacteria increases (and the resistance decreases) in an exponential manner in the absence of ampicillin, and remains constant where ampicillin is present, even though the wells were seeded with equal numbers of bacteria. From these data, it is apparent that the antibacterial effect of the growth inhibiting substance (in this case ampicillin) can be readily detected, and generally in less than one hour. These data indicate that, in accordance with the invention, it is possible to rapidly monitor bacterial growth of log phase growing wells, and confirms that the positive control (in this case ampicillin) works. It is noted that for wells containing 30 μl volume (which is equivalent to the wells on a 384 microtiter plate), more than 3,000 wells may be readily integrated onto a single glass base plate, enabling the convenient screening of 30,000 wells or more each day.

The log phase growth can be readily determined from the data, e.g., by a computer program that computes the logarithm of the capacitance or resistance change data and determines the slope of the linear portion of the resulting data (i.e., the exponential growth portion). The data may also be plotted on semi-logarithmic paper and a linear fit done to the portion of the curve that is most linear after the initial lag phase to determine the slope of the log growth curve.

The present invention is well suited to systematic searching for new antibiotic substances from novel biological and chemical sources. For example, fermentation broths of libraries of E. coli and Bacillus subtilis which carry large genomic segments from soil microbes (termed "metagenomic libraries") and collections of small, organic molecules can be screened for inhibitors of bacterial cell growth. Target cells to be screened can include wild-type and several enfeebled strains of E. coli 0157:H7. An example of a source of such target materials are collections available from Nanosyn (Tucson, Ariz.) which comprise a collection of 26,000 compounds maintained in dimethyl sulfoxide (DMSO) stocks and distributed in 96 well microtiter plates. Liquid chromatography/mass spectrometry analytical data are available for each compound to confirm its structure, purity, and solubility. This collection is composed of a large array of molecules collected from academic and commercial sources, with a molecular weight range of 300 to 600 daltons and pLog values, much like the top 300 selling drugs. Since only a small volume of such compound is added directly to the culture wells, the concentration of DMSO in any well will be too low to interfere with bacterial growth. Positive "hits" from the collection can then be analogued and retested to create a structure-activity relationship. The probability of finding new chemistry can be maximized utilizing gene expression. This may be done by constructing a library of metagenomic DNA from soil in a shuttle vector that moves by conjugation from E. coli to Bacillus subtilis. Genes from diverse prokaryotes (such as Thermotoga, Synechocystis, Chromatium, Clostridium, Lactobacillus, Corynebacterium, Bacteroides, and Leptospira) have been expressed in E. coli either from their own promoters or from promoter-like sequences present within the cloned DNA. These species represent seven different phyla of bacteria, demonstrating that E. coli can utilize a very wide diversity of heterologous gene expression signals. To expand the range of gene expression, a clone bank can be moved into B. subtilis, which differs from E. coli in GC content, promoter structure, cell surface structure and permeability, and genetic regulatory mechanisms. The DNA can be cloned in vectors that can be moved from E. coli to other bacteria and screened again. In this manner, it is possible to obtain products expressed in E. coli, and then to obtain a different set of products through genes expressed in Bacillus. Vectors can be constructed that shuttle easily between E. coli and Bacillus by a simple mating or conjugation. A library may be constructed utilizing proven methods for DNA isolation, purification, sizing and cloning in the shuttle vector. The library can be moved from E. coli to B. subtilis by arrayed mating, which means that the library can be arrayed in E. coli and then replicated into a lawn of B. subtilis containing the appropriate antibiotic selections, and the colonies that grow represent transconjugants of B. subtilis containing the clones. Such a method facilitates efficient screening of the same library in E. coli and B. subtilis, and it keeps all of the clones arrayed so that it is possible to follow the activity of each bacterial artificial chromosome (BAC) in E. coli and B. subtilis, and the clones can be handled with a 96-prong replicator, avoiding the necessity of individual matings.

In accordance with the invention, such formatted chemical and natural product libraries can be readily examined. An exemplary process for doing so is illustrated in FIGS. 7A–7D. A base plate 21 is utilized having a plurality of microwells 22 formed therein, preferably in a rectangular matrix pattern. As noted above, it is preferable that the wells have a volume of 30 $\mu$l or less, and most preferably have volume capacities of a few tens of nanoliters. Exemplary dimensions are shown for the wells 22 in FIG. 6A (a depth of 100 $\mu$m and an average well diameter of 300 $\mu$m providing a well volume in the range of 10 nl). The surfaces of the wells 22 are preferably hydrophilic, while "land" areas 45 between the wells are most preferably formed to be hydrophobic. Such surface properties can be obtained, for example, by forming the base plate 21 of a normally hydrophobic polymer material, such as polydimethylsiloxane (PDMS), and then coating or treating the surfaces of the wells 22 to be hydrophilic. Such surface characteristics help to confine the liquid applied to the base plates to the wells and to minimize cross-contamination of the contents from one well to an adjacent well.

To carry out a test, the base plate 21 is dipped in a dilute solution of bacteria, thereby filling the individual wells 22, as illustrated in FIG. 7B. The excess solution is then removed from the array, e.g., by being "squeegied off" of the top surface of the array where the surface areas 46 are hydrophobic. The wells in the base plate are now uniformly filled with the solution containing the bacteria and growth medium. If the test is to be carried out at a later time (e.g., after a large group of plates has been prepared), the base plate with the solution in the wells may be maintained at an appropriate temperature to retard growth of the bacteria (e.g., 4° C.) and is preferably maintained in a humid chamber to minimize evaporation. The liquid samples to be tested for effect on the bacteria can now be transferred to specific wells, e.g., from a master plate using a Tecan or Packard Biosciences robotic spotter, which, as illustrated schematically at 50 in FIG. 7C, transfers controlled amounts of the sample liquids from an array of pipettes 51 to the wells 22. The array of pipettes 51 is preferably formed to precisely match the array of wells 22, allowing simultaneous discharge of liquid from the array of pipettes into multiple wells 22. Alternatively, the sample liquids can be supplied to the wells 22 one at a time or one row of wells at a time, etc. The transfer of liquid preferably is carried out in a humid chamber to minimize evaporation. The base plates 21 are then warmed to an appropriate growth temperature (e.g., 37° C.) in a humid chamber to promote growth of the bacteria. Preferably, the atmosphere within the chamber can be controlled, including control of the oxygen content within the growth chamber. The growth in numbers of bacteria in each row is then monitored over time (typically over a period of 2–4 hours) as discussed above, yielding growth curves as schematically illustrated at 53, 54, and 55 in FIG. 7D. The curves 53 and 54 illustrate wells in which the sample liquid had substantially no effect on bacteria growth, while the curve 55 shows a well in which the growth of bacteria has been inhibited. The collection, analysis, and display of the data may be carried out under the control of the computer 41. Preferably, several control wells 22 are provided in which the contents consists of bacterial cultures grown in the absence of and in the presence of known antibiotics (e.g., tetracycline, streptomycin, ampicillin, and nalidixic acid). The cell growth in such small wells with common bacterial strains such as E. coli occurs very rapidly, without the typical lag time seen in large cultures. For example, for E. coli cultured in a well 22 having about 10 nanoliters of contents, the bacterial culture will saturate when there are about 1,000 cells present. If the well is initially inoculated with 50–100 cells, saturation will occur in three to four generations, with a doubling time of about 20 minutes. Thus, within wells in which the growth of bacteria is not inhibited, saturation will occur in one to two hours, establishing a baseline time for growth to saturation for the "control" wells. Thus, wells in which bacterial growth does not occur or in which growth is suppressed compared to the control wells due to the antibacterial action of the substance added to the well will be detectable within two hours, far sooner than with the use of conventional bacterial culture techniques.

As an example of the use of the invention, screening can be carried out with a "learning set" of metagenomic samples, for example, clones that have hemolytic activity, which have the advantages, first, that such clones express genes and, therefore, have a better chance of containing active compounds than clones for which there is no indication of gene expression; secondly, compounds with one biological activity often have another, seemingly unrelated activity; and, further, one of the hemolytic clones has already been shown to produce a novel compound that has both hemolytic and antibiotic activity. The learning set of samples may also contain a plate of clones with no known activity chosen randomly from among the non-hemolytic clones. The learning set may then be used to de-bug the assay to gain experience in handling the clones and to follow growth by three parallel parameters. Challenges to be confronted in such processes involve the introduction of bacterial cells with the samples to be tested, because the sample itself is a bacterial culture. It may be expected that a strain containing the BAC will be resistant to any antibiotic produced because antibiotic biosynthetic pathways are invariably linked to the appropriate resistance gene which the target strain of E. coli will, presumably, not contain. Thus, the growth of the producing strain could obscure effects on growth of the target strain. This can be addressed by either removing the bacterial cells from the samples to be tested, testing ethyl acetate extracts of the cultures, or incorporating in the growth medium an antibiotic that inhibits growth of the producing strain and not the target strain. By developing screening that is repeatable and routine, the screening of the entire metagenomic library can be carried out. It is expected that any compounds with antimicrobial activity will slow or inhibit the growth of bacteria, and thus any compounds that inhibit growth by 20% or more are preferably retested over a range of concentrations both in the arrays and in culture tubes. Filters may also be soaked with the positive compounds and placed in the center of petri plates to allow examination for a zone of inhibition. If, after these further tests, the compounds are still found to be positive, the range of antimicrobial activity on other bacteria than E. coli can then be tested. After passing through such screening, the active compounds can then be tested to determine if they lyse red blood cells. For any compounds in the chemical library found to be positive, analogs of the compounds can be tested, if available, to look for a structure-activity-relationship. Additional analogs of the active compound can be synthesized to determine whether the effectiveness or specificity of the compound can be improved. If a fermentation broth is shown to be positive upon retesting, additional steps can be taken.

Because the present invention allows the detectable growth of bacterial cultures in very short periods of time (two hours or less) under favorable growth conditions, the invention is also well suited to investigate the effects of varying the environmental conditions, e.g., ambient temperature, nutritional content of the growth medium, and ambient atmosphere. $E.$ $coli$ in its natural environment can survive within a broad range of physical and nutritional conditions. Because it is unclear when many gene products are expressed, the larger the number of growth opportunities that can be performed on a mutant strain, the greater the opportunity for discovery of phenotypic differences between strains that will aid in describing gene function. For example, growth kinetics can be tested in media that provide different carbon, nitrogen, and phosphorus sources as well as growth inhibitors, and in media with different pH and salinity. Since some growth phenotypes may be revealed only under particular physical conditions, base plates containing wells inoculated with bacteria can have their growth monitored at various temperature and oxygen concentration conditions. As an example, for bacterial strains grown in 200 different media, under three different temperatures, and at three different oxygen concentrations, a total of 1,800 observations are required to evaluate the phenotype of each strain. To carry out such tests using conventional growth culture techniques could be prohibitively expensive and time consuming, but can be readily accomplished in relatively short periods of time utilizing the present invention.

Figure 7:
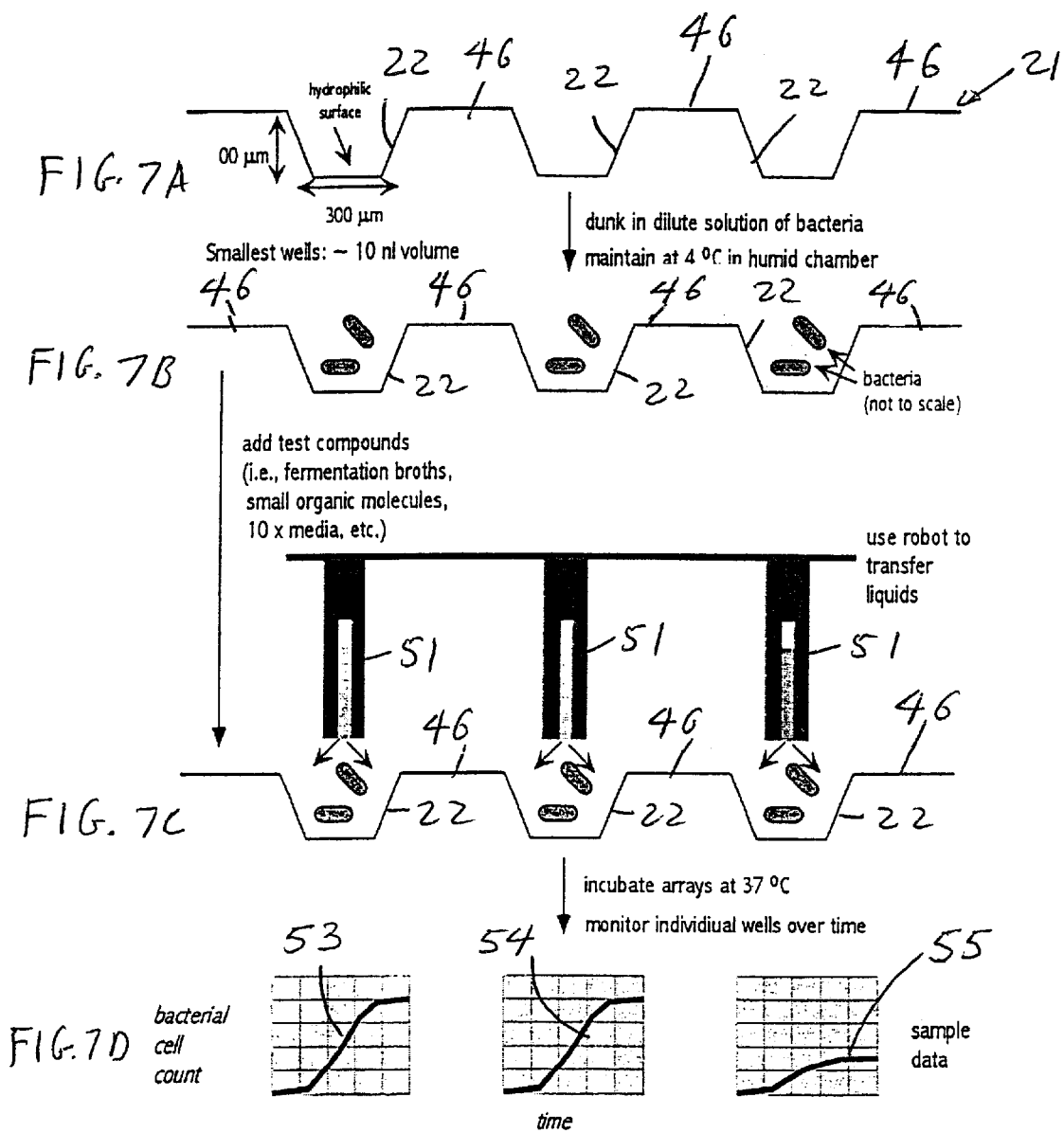
FIGS. 7A–7D are schematic illustrations of a bacterial growth assay process.
Figure 8:
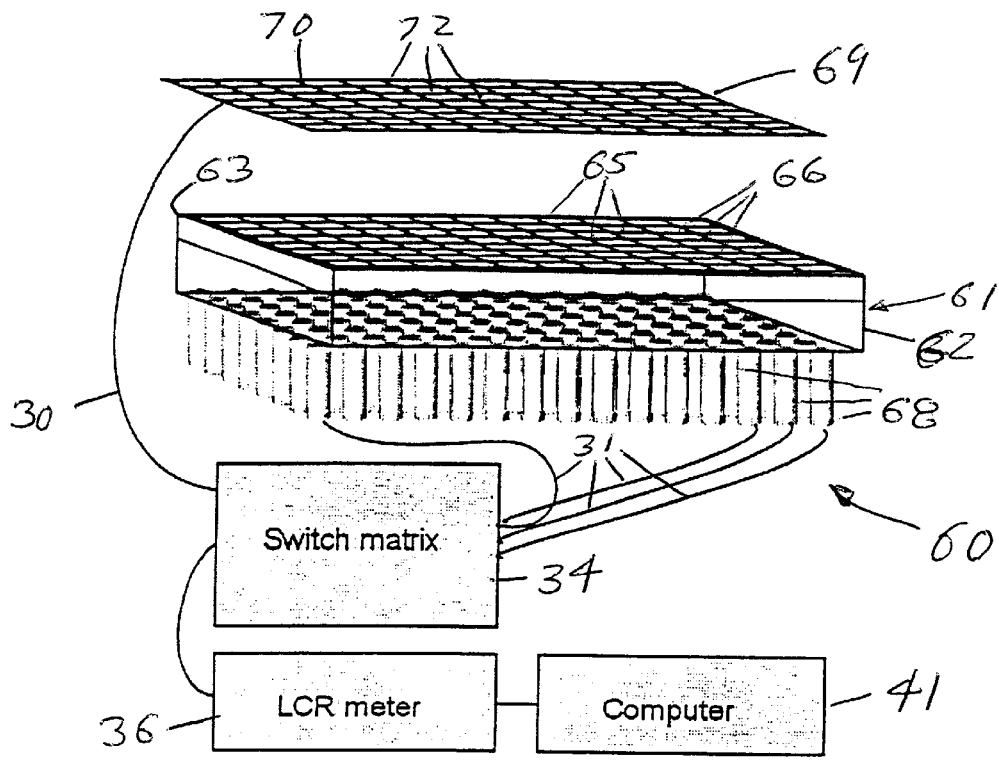
FIG. 8 is a simplified diagram of a further embodiment of microbial growth assay apparatus in accordance with the invention.
Figure 9:
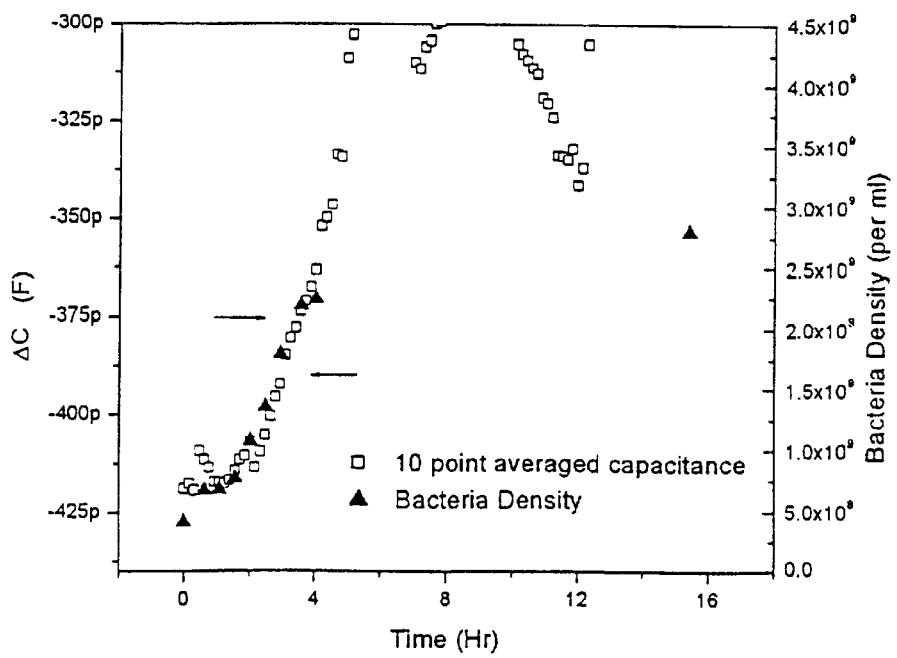
FIG. 9 is a graph showing data for a growth test utilizing the apparatus of FIG. 1 comparing optical turbidity data to change in capacitance between the electrodes as measured at a frequency of 75 kHz.
Figure 11:
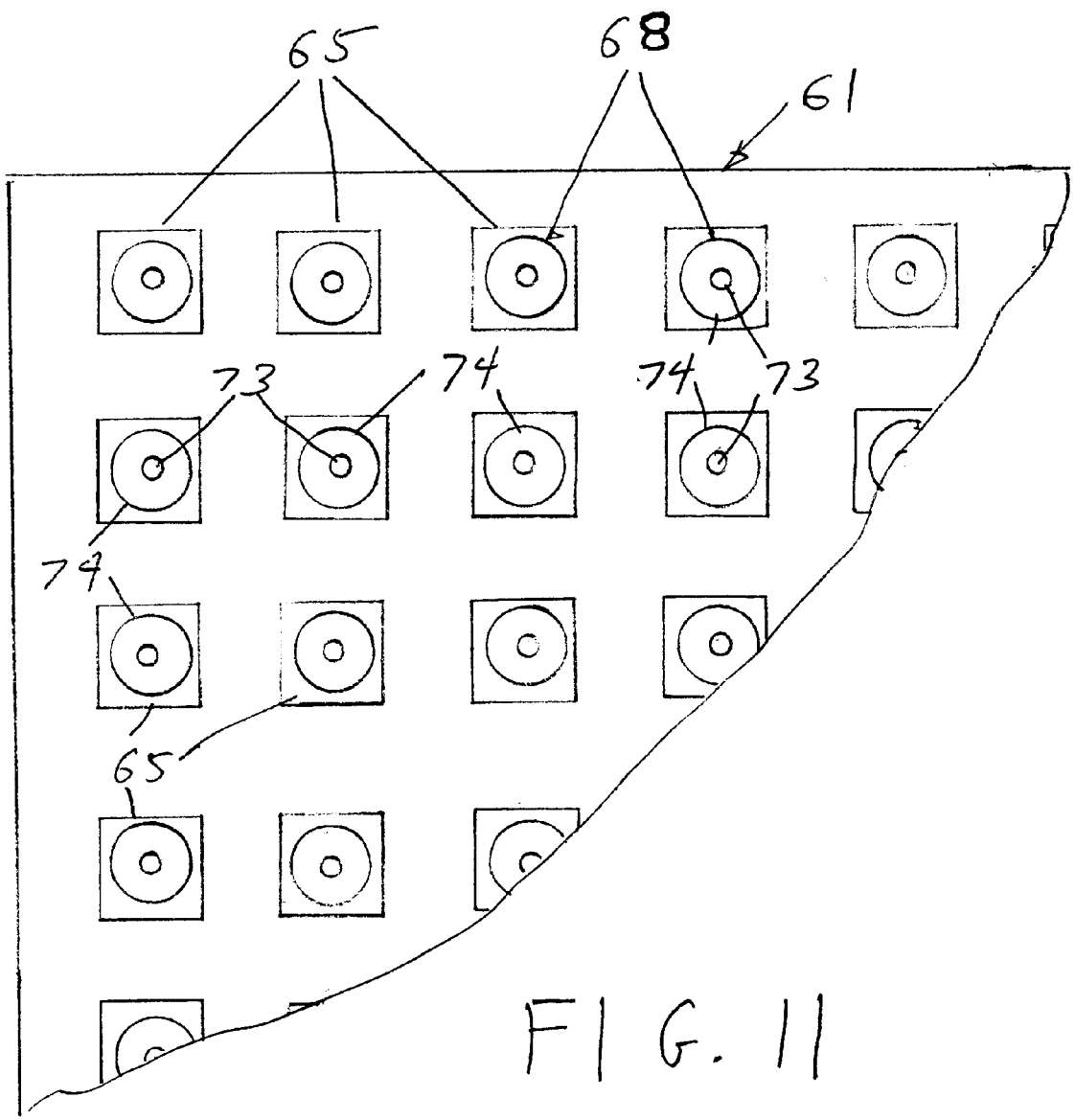
FIG. 11 is a plan view of a microbial growth assay apparatus having coaxial electrodes.

A further embodiment of microfabricated microbial growth assay apparatus in accordance with the invention that is well suited to scaling up the number of wells per base plate is shown generally at 60 in FIG. 8. The apparatus 60 has a base plate 61 formed of a glass foundation plate 62, such as a conventional silica glass slide, on which is formed a layer of formable polymer plastic 63, e.g., PDMS, in which is molded an array of micro wells 65 which are spaced from one another by land areas 66. An array of coaxial tips 68 is positioned at the bottom of the glass foundation plate 62, with each of the coaxial tips located under one of the microwells 65. The coaxial tips 68 are connected by wires 31 which extend back from each tip 68 to a switch matrix unit 34. A cover slip plate 69, which may have an integral counter electrode 70 formed on it, is mounted over the wells 65 after the wells have been filled. The electrically conductive counter electrode 70 is electrically connected by the wire 30 to the switch matrix 34. A single electrical counter electrode 70 can be used to provide the counter electrode for each of the wells since each of the coaxial tips 68 in the array is individually connected to the switch matrix 34. The cover slip 69 can be formed as, for example, a thin sheet of polymer (e.g., PDMS) or glass on the surface of which the electrode 70 is formed as a thin metal layer (e.g., gold, copper or aluminum) secured by gluing to the surface of the cover slip plate or as a conductive layer (e.g., gold) deposited on the surface in various ways and lithographically patterned by etching as desired, etc. Preferably, the cover slip plate is transparent and the counter electrode 70 is patterned with openings 72 which provide optical access holes to allow for optical density and epifluorescence measurements. As shown in FIG. 11, each of the coaxial electrodes 68 has an inner electrode 73 and a coaxial outer electrode 74 that surrounds and is spaced from the inner electrode 73. The capacitance between the inner electrode 73 and the outer electrode 74 at each of the coaxial tip electrodes 68 and/or between the electrodes 68 and the counter electrode 70 is measured by scanning, using the switch matrix 34 as discussed above, in a relatively short period of time by applying a signal by the wires 31 to each of the coaxial tips 68 (each wire 31 may comprise a coaxial cable). The capacitance between the electrodes 68 and 70 will be affected by the dielectric characteristics of the contents of the microwell that is between these electrodes. The wells 65 can be formed as square or rectangular as shown in FIGS. 7, 8 and 11, which allows for maximum well volume per unit area, or the wells can be formed in circular or other configurations if desired. Use of the cover slip 69 is also preferred because the sealing provided by the cover slip eliminates or minimizes evaporation, further facilitating large scale screening. Although the embodiment of the base plate 60 shown in FIG. 8 does not carry out resistance measurements of the contents of the microwells, the effect of capacitance changes are readily detected and electromagnetic shielding is facilitated by the arrangement shown in this figure. The inner and outer electrodes 73 and 74 may also be formed to be in electrical contact with the contents of the wells to carry out resistance measurements. To verify the correlation between changes in capacitance and other methods for measuring bacterial cell density, it is preferable to be able to also measure the optical turbidity of the contents of the individual microwells. The base plate structure 60 facilitates such optical examination because of the transparency of the glass foundations 62, the molded layer 63, and the cover slip 69 (with the optical access openings 72 provided in the electrode 70). For example, the capacitance measurements can be carried out simultaneously with monitoring of optical density (e.g., using illumination at 600 nm) and by measuring fluorescence. A measurement of fluorescence can be made possible by the insertion of the GFP gene coupled to a strong, constitutive promoter, into the $E.$ $coli$ chromosome. When GFP is expressed, the cells accumulate the stable green fluorescent protein. Because the gene is expressed steadily at all stages of growth, the amount of fluorescence is proportional to the cell member. FIG. 9 shows the results of tests comparing optical turbidity to increase in capacitance between the two electrodes at a well of the type as shown in FIG. 1 at 75 kHz. The optical density of a single well was measured over time at 600 nm wavelength and converted to the number of bacteria per milliliter (scale on right hand side of the graph). The capacitance of the well was measured as discussed above with respect to the apparatus 20 of FIG. 1 (capacitance scale on the left hand side of the graph), and the capacitance data were normalized to a control well containing only Luria broth. These data show that the measured capacitances correlate almost exactly with optical measurements of bacterial density during the initial log phase growth of the culture within the well.

Figure 10:
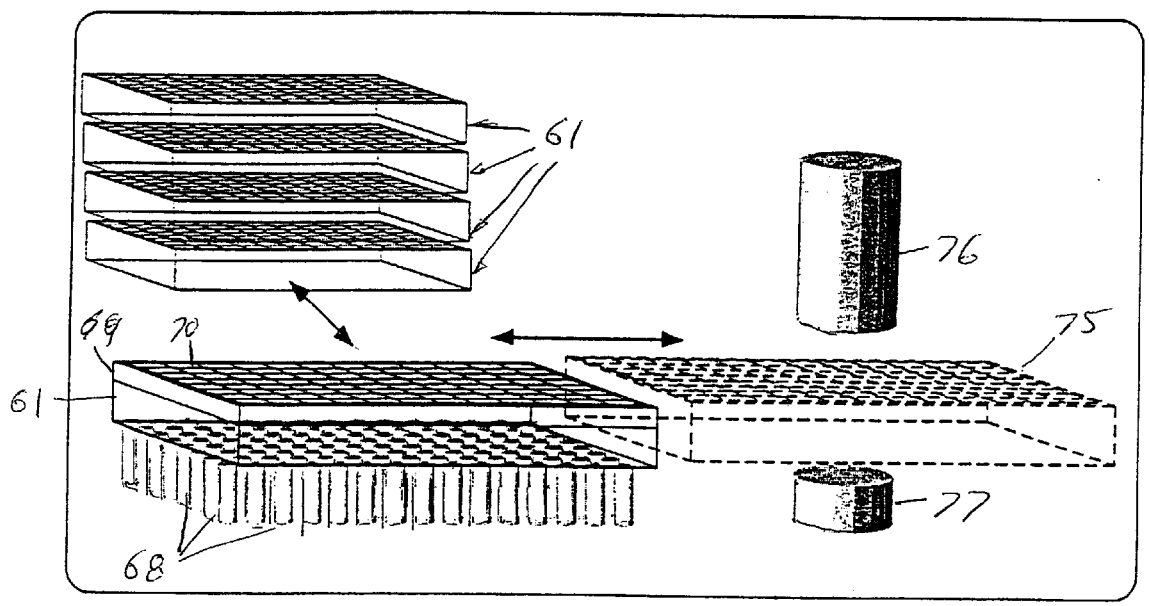
FIG. 10 is an illustrative diagram showing the use of the assay apparatus of FIG. 8 in an automated reading apparatus which obtains both capacitance and optical measurements of growth in the microwells of the assay apparatus.

As illustrated in FIG. 10, the base plates 61 of FIG. 9 are readily adapted to be used in multi-functional plate readers. A base plate 61 can be fed from a stack of such plates to a position in which it is mounted onto an array of coaxial tips 68. In the structure as shown in FIG. 10, the coaxial tips 68 are fixed in place in their positions in the array, and an individual base plate 61 is precisely aligned in position onto the tips 68, with the tips engaged with the bottom of the base plate 61, each tip aligned under a well. An electrical connection is then made to the entire electrode 70 on the base plate, e.g., by engaging a conductive metal finger into electrical contact with the electrode 70, followed by the selective measurement of the capacitance and/or resistance of each well as discussed above. After completion of the capacitance and/or resistance measurements, the base plate 61 can then be moved to a position indicated generally at 75 in FIG. 10, within an optical inspection system which includes, e.g., a microscope objective 76 above the base plate and an optical detector 77 below the base plate, to allow microscopic inspection of each of the individual wells in the base plate. The data from the optical measurements can then be correlated with the corresponding data for each well from the capacitance measurements. Thus, no permanent electrical contacts are required to the base plates 61, and the system not only allows shuttling of base plates between the electrical and optical readout positions, but also the ability to pull the base plates from the stack or to organize them on a planar belt or carousel for highly automated reading and handling. In addition, a robotic spotting system, as discussed above, may be readily integrated with the optical and capacitive readers illustrated in FIG. 10.

It is understood that the invention is not confined to the particular embodiments set forth herein as illustrative, but embraces all such forms that come within the scope of the following claims.

What is claimed is:

1. Microbial growth assay apparatus comprising:
   (a) a base plate having a top surface, a plurality of microbial growth assay wells formed as depressions in the base plate which extend below the top surface, each well having a liquid capacity of 30 $\mu$L or less; and
   (b) electrodes capacitively coupled through the wells and electrical connectors connected to the electrodes, wherein a first electrode for each well is under the well and a second electrode for each well is on a cover mounted over the base plate such that a capacitor is formed between the first and second electrodes for each well with the contents of the well between the electrodes, whereby the effect of the contents of the wells may be measured by measuring the capacitance between the electrodes at each well.

2. The apparatus of claim 1 wherein the base plate is formed of a material selected from the group consisting of glass, quartz, plastic, silicon and combinations thereof.

3. The apparatus of claim 1 further including a meter that measures capacitance and a switching unit, the switching unit electrically connected to the meter and electrically connected individually to the electrodes for each of the plurality of wells, the switching unit switchable to selectively connect the electrodes for one of the wells at a time to the meter.

4. The apparatus of claim 3 wherein the meter further includes an inductance and resistance meter electrically connected to the switching unit.

5. The apparatus of claim 3 further including a computer connected to the meter and to the switching unit to provide control signals to the switching unit and to the meter to control the connection of the electrodes from individual wells to the meter and to receive a signal from the meter for each well that is coordinated with the switching of the switching unit to connect the electrodes for the well to the meter.

6. The apparatus of claim 1 wherein the first of the electrodes at each well comprises a coaxial tip electrode comprising an inner electrode and an outer electrode that surrounds and is spaced from the inner electrode, the coaxial tip electrode disposed beneath the well and further wherein the second electrode comprises an electrically conductive layer on the cover.

7. The apparatus of claim 6 wherein areas of the cover are substantially transparent such that the contents of the wells can be optically inspected through the cover.

8. The apparatus of claim 1 wherein there are at least 100 assay wells formed on the base plate.

9. The apparatus of claim 1 wherein the surfaces of the depressions forming the wells are hydrophilic and the areas of the top surface of the base plate between the wells are hydrophobic.

10. The apparatus of claim 1 wherein the wells are arranged on the base plate in a rectangular matrix pattern.

11. Microbial growth assay apparatus comprising:
    (a) a plurality of microbial growth assay wells, each well having a selected liquid capacity; and
    (b) electrodes capacitively coupled together through the wells and electrical connectors connected to the electrodes, wherein the electrodes for each well comprise an inner electrode and a coaxial outer electrode that surrounds and is spaced from the inner electrode.

12. The apparatus of claim 11 wherein the wells are formed on a base plate having a top surface as depressions in the base plate which extend below the top surface.

13. The apparatus of claim 11 wherein the wells are arranged on the base plate in a rectangular matrix pattern.

14. The apparatus of claim 11 wherein the inner electrode and outer electrode for each well are mounted to be in electrical contact with the liquid contents of the well to thereby allow capacitance or resistance measurements or both of the contents between the electrodes.

15. The apparatus of claim 11 wherein the selected liquid capacity of each well is 30 $\mu$l or less.

16. Microbial growth assay apparatus comprising:
    (a) a plurality of microbial growth assay wells, each well having a selected liquid capacity; and
    (b) electrodes coupled together through the wells and electrical connectors connected to the electrodes, wherein the wells are formed on a base plate having a top surface, wherein first and second electrodes are formed on the top surface of the base plate for each well, the first and second electrodes each having an apex reaching a point, the points of the apexes of the first and second electrodes facing each other such that the points of the first and second electrode can be in electrical contact with liquid contents in the well to thereby allow both capacitance and resistance measurements of the contents between the first and second electrodes for each well.

17. The apparatus of claim 16 wherein the wells are formed on a base plate having a top surface as depressions in the base plate which extend below the top surface.

18. The apparatus of claim 17 wherein the base plate is formed of a material selected from the group consisting of glass, quartz, plastic, silicon, and combinations thereof.

19. The apparatus of claim 16 wherein the wells are arranged on the base plate in a rectangular matrix pattern.

20. The apparatus of claim 16 wherein the selected liquid capacity of each well is 30 $\mu$l or less.

21. The apparatus of claim 16 further including a meter that measures capacitance, and a switching unit, the switching unit electrically connected to the meter and electrically connected individually to the electrodes for each of the plurality of wells, the switching unit switchable to selectively connect the electrodes for one of the wells at a time to the meter.

* * * * *